(12) United States Patent
Taravella et al.

(10) Patent No.: US 7,611,727 B2
(45) Date of Patent: Nov. 3, 2009

(54) PHARMACEUTICAL COMPOSITION FOR TRANSDERMAL OR TRANSMUCOUS ADMINISTRATION

(75) Inventors: Brigitte Taravella, Paris (FR); Valérie Masini-Eteve, Verrieres le Buisson (FR)

(73) Assignee: Besins International Belgique, Drogenbos (BE)

( * ) Notice: Subject to any disclaimer, the term of this patent is extended or adjusted under 35 U.S.C. 154(b) by 566 days.

(21) Appl. No.: 10/436,380

(22) Filed: May 12, 2003

(65) Prior Publication Data

US 2004/0175416 A1 Sep. 9, 2004

(30) Foreign Application Priority Data

Feb. 20, 2003 (FR) .................................. 03 02083

(51) Int. Cl.
*A61F 13/00* (2006.01)
(52) U.S. Cl. ..................................................... 424/449
(58) Field of Classification Search ................. 424/449
See application file for complete search history.

(56) References Cited

U.S. PATENT DOCUMENTS

| | | | |
|---|---|---|---|
| 4,906,169 A | | 3/1990 | Chien et al. |
| 5,332,577 A * | | 7/1994 | Gertner et al. ............... 424/449 |
| 5,788,984 A | | 8/1998 | Guenther et al. |
| 5,891,462 A | | 4/1999 | Carrara |
| 6,582,724 B2 * | | 6/2003 | Hsu et al. .................... 424/449 |
| 2003/0175329 A1 * | | 9/2003 | Azarnoff et al. ............. 424/449 |
| 2004/0001881 A1 * | | 1/2004 | Selzer et al. ................. 424/449 |
| 2004/0110732 A1 * | | 6/2004 | Masini-Eteve et al. ...... 514/170 |

FOREIGN PATENT DOCUMENTS

| | | |
|---|---|---|
| EP | 0 364 211 A1 | 4/1990 |
| EP | 0 672 422 | 3/1994 |
| EP | 0 737 477 A1 | 10/1996 |
| EP | 1 043 020 A1 | 10/2000 |
| EP | 0 811 381 B1 | 5/2003 |
| FR | 2518879 A | 7/1983 |
| FR | 2814074 A1 | 3/2002 |
| JP | 2002-212105 | 7/2002 |
| RU | 2122396 C1 | 11/1998 |
| WO | WO 92/07590 A1 | 5/1992 |
| WO | WO 94/04157 A1 | 3/1994 |
| WO | WO 95/17896 A1 | 7/1995 |
| WO | WO 97/39743 A1 | 10/1997 |
| WO | WO 98/18417 A1 | 5/1998 |
| WO | WO 98/32465 A1 | 7/1998 |
| WO | WO 99/24041 | 5/1999 |
| WO | WO 02/11768 A1 | 2/2002 |
| WO | WO 02/22132 A2 | 3/2002 |
| WO | WO 02/22132 A3 | 3/2002 |

OTHER PUBLICATIONS

XP002260254, Database WPI.
XP002260255, Database WPI.
Van Scott et al., "Typerkeratinization, Comeocyte Cohesion, and Alpha Hydroxy Acids," J. Am Acad Dermatol 11:867-879 (1984).
Office Action issued Jun. 11, 2007 in U.S. Appl. No. 10/393,077 (9 pgs.).
Office Action issued Oct. 20, 2006 in U.S. Appl. No. 10/393,077 (9 pgs.).
Office Action issued Jan. 26, 2006 in U.S. Appl. No. 10/393,077 (15 pgs.).

* cited by examiner

*Primary Examiner*—M P Woodward
*Assistant Examiner*—Bethany Barham
(74) *Attorney, Agent, or Firm*—Foley & Lardner LLP

(57) ABSTRACT

The present invention relates to a novel pharmaceutical composition for transdermal or transmucous administration of at least one active substance, and comprising especially a fatty acid as a percutaneous absorption promoter, at least one alcoholic vehicle and also a stabilizer capable of stabilizing the fatty acid in the said pharmaceutical composition.

34 Claims, No Drawings

PHARMACEUTICAL COMPOSITION FOR TRANSDERMAL OR TRANSMUCOUS ADMINISTRATION

The present invention relates to a novel pharmaceutical composition for transdermal or transmucous administration of at least one active substance, and comprising in particular a fatty acid as percutaneous absorption promoter, as well as a stabilizer capable of stabilizing the fatty acid in said pharmaceutical composition.

It is well known that certain active substances are not suitable for oral administration for various reasons associated, inter alia, either with a high level of metabolism in the liver: "1st passage effect"; or with a high level of gastrointestinal degradation.

Transdermal or transmucous formulations have thus been developed in order to circumvent these drawbacks.

Specifically, pharmaceutical compositions for transdermal or transmucous administration have several advantages over oral forms: elimination of the problem of metabolism of the active substance by the liver, no gastric degradation of the active substance, possible reservoir effect with continuous release of the active principle over time. However, they may pose problems as regards the passage of the active substances through the skin.

In fact, active substances do not all diffuse through the percutaneous barrier in a similar manner. This diffusion depends on the chemical and physicochemical characteristics of the molecule.

In order to facilitate this passage of the active substances through the skin, transdermal or transmucous formulations may include specific molecules known as "percutaneous absorption promoters". This name is given to any molecule that promotes the reversible diffusion of an active principle through the skin or mucous membranes, and any solubilizing agent that promotes the partition of the active principle between the vehicle and the horny layer of the epidermis or of the mucous membranes. One of the classes of absorption promoters commonly used in transdermal or transmucous formulations is the class of fatty acids.

However, the Applicant Company has shown that aqueous-alcoholic compositions containing these fatty acids are not chemically stable. Specifically, on account of its "acid" function and in the presence of alcohol, the fatty acid undergoes an esterification reaction according to the laws of organic chemistry. Thus, for example, oleic acid is converted into ethyl oleate in the presence of ethanol.

However, since medicinal products are often stored for a certain amount of time before being sold, it is essential for their composition to be invariable so as to ensure patient health safety. Any medicinal product must therefore demonstrate high stability, i.e. its composition must not vary over time. Stability of the pharmaceutical composition is a guarantee of consistency in terms of bioavailability of the active agent, efficacy of the pharmaceutical composition, and acceptability and harmlessness of the medicinal product for the patient.

Thus, in a gel or an aqueous-alcoholic solution, if there is appreciable degradation of the fatty acid, acting as percutaneous absorption promoter of the active substance, this may considerably change the bioavailability of the active substance and thus its efficacy.

The Applicant Company has performed extensive studies and research in order to provide a solution to this problem of stability of fatty acids in alcoholic medium, in order to obtain satisfactory stability.

The Applicant Company has thus found that it is possible to stabilize the fatty acid in the pharmaceutical composition by adding a buffer and/or by adding small amounts of an ester of the corresponding acid, at the time of preparation of said pharmaceutical composition.

The invention thus relates to a pharmaceutical composition for transdermal or transmucous administration of at least one active substance, comprising at least one fatty acid as percutaneous absorption promoter, at least one alcoholic vehicle, and also at least one stabilizer capable of stabilizing the fatty acid in the said pharmaceutical composition.

In the context of the present invention, the term "stable" means a pharmaceutical composition whose qualitative and quantitative composition and whose physical, chemical and biological characteristics do not change significantly over time under given temperature and humidity conditions, i.e. for 3 years at 25° C./60% RH, for 1 year at 30° C./65% RH and/or for 6 months at 40° C./75% RH.

The term "significant change" means any qualitative and/or quantitative change, and also any change in the physical, chemical and biological characteristics that takes place outside the acceptance criteria defined for the analytical method used for each chemical, physical or biological test (numerical limit, interval or other relevant measurement).

The percutaneous absorption promoter(s) included in the pharmaceutical composition according to the invention is (are) preferably selected from the group consisting of saturated and unsaturated fatty acids.

They are preferably long-chain aliphatic fatty acids containing from 10 to 18 carbon atoms. The fatty acids are selected, in a non-limiting manner, from the group consisting of capric acid (10:0), lauric acid (12:0), myristic acid (14:0), palmitic acid (16:0), stearic acid (18:0); oleic acid (18:1), palmitoleic acid (16:1), linoleic acid (18:2) and linolenic acid (18:3).

The fatty acid content in the pharmaceutical composition according to the present invention will advantageously be between 0.1% and 20%, preferably between 0.2% and 10% and even more preferably between 0.5% and 5%, these percentages being expressed by weight relative to 100 g of pharmaceutical composition.

However, it is explicitly indicated here that the pharmaceutical composition according to the invention may contain other percutaneous absorption promoters in combination with the fatty acid(s).

The stabilizer is selected from the group consisting of buffers and/or fatty acid esters corresponding to the fatty acids present in the pharmaceutical composition as percutaneous absorption promoters.

When they are present in the pharmaceutical composition according to the invention, the buffer(s) advantageously make it possible to maintain the pH of the said composition between 4 and 10, preferably between 5 and 9 and even more preferably between 6 and 8.

The buffer content of the pharmaceutical composition according to the invention is advantageously between 1% and 80%, preferably between 5% and 70% and even more preferably between 10% and 50%, these percentages being expressed on a weight basis relative to 100 g of pharmaceutical composition.

According to one preferred embodiment of the pharmaceutical composition according to the invention, the buffers are selected from the group consisting of:

basifying or basic buffers such as a phosphate buffer (for example dibasic or monobasic sodium phosphate), a citrate buffer (for example sodium citrate or potassium citrate), sodium carbonate, sodium bicarbonate, a mixture of sodium carbonate and sodium bicarbonate being preferable, or neutral buffers such as a Tris buffer, preferably a phosphate buffer.

According to another embodiment of the pharmaceutical composition according to the invention, the saturated or unsaturated fatty acid ester(s) used is (are) those that would result from the reaction between a fatty acid identical to that contained in the said composition, with an alcohol identical to that contained in the said composition. The fatty acid esters are thus preferably selected from the group consisting of ethyl oleate, isopropyl oleate, isopropyl myristate, isopropyl palmitate, ethyl octanoate, ethyl dodecanoate, ethyl linoleate and ethyl linolenate.

The content of fatty acid ester added as stabilizer in the pharmaceutical composition according to the invention is advantageously between 0.1% and 10%, preferably between 0.2% and 5% and even more preferably between 0.5% and 2.5%, these percentages being expressed on a weight basis relative to 100 g of pharmaceutical composition.

The pharmaceutical composition according to the invention also contains a non-aqueous vehicle of alcohol type. The alcoholic vehicle must be capable of dissolving all the components of the formulation and especially the fatty acid and the possible ester thereof. Preferably, the alcoholic vehicle may be selected from ethanol and/or isopropanol. However, ethanol represents a preferred vehicle according to the invention since it contributes efficiently to the transcutaneous passage of the active principle by evaporating quickly on contact with the skin.

The alcohol content is advantageously between 10% and 90%, preferably between 20% and 80% and even more preferably between 40% and 70%, these percentages being expressed on a weight basis relative to 100 g of pharmaceutical composition.

The pharmaceutical composition according to the invention may also comprise an aqueous vehicle. The aqueous vehicle makes it possible to dissolve the hydrophilic molecules contained in the formulation and also promotes the diffusion of the lipophilic molecules of the formulation towards the horny layer. It forms a binary vehicle with the non-aqueous solvent.

The aqueous vehicle will preferably be water. Its content is between 1% and 80%, preferably between 10% and 70% and even more preferably between 20% and 60%, these percentages being expressed on a weight basis relative to 100 g of pharmaceutical composition.

The pharmaceutical composition according to the invention may also contain a co-solvent such as polyols or polyglycols such as, for example, glycerol, propylene glycol or polyethylene glycol for a content of between 0.5% and 20%, and preferably between 1% and 10%, these percentages being expressed on a weight basis relative to 100 g of pharmaceutical composition. The co-solvent makes it possible to increase the solubility of the active substances.

The pharmaceutical composition according to the invention may be in the form of a gel, a solution, a cream, a lotion, a milk, an ointment, an aerosol or a patch.

It is preferably in the form of a gel or a solution.

When the pharmaceutical composition according to the invention is in the form of a gel, it also comprises a gelling agent.

Advantageously, and depending on the type of gelling agent used, it has a content of between 0.2% and 30% of a gelling agent, preferably between 0.5% and 10% and even more preferably between 0.3% and 5%, these percentages being expressed on a weight basis per 100 g of pharmaceutical composition.

Carbomers or polyacrylic acids such as Carbopol 980 or 940 NF, 981 or 941 NF, 1382 or 1382 NF, 5984, 2984 or 934 NF, Pemulen TR1 NF or TR2 NF, Ultrez, Synthalen CR, non-preneutralized acrylic polymers; cellulose derivatives such as ethyl cellulose, hydroxypropyl cellulose, hydroxyethyl cellulose, hydroxypropylmethyl cellulose (HPMC), carboxymethyl cellulose (CMC), etc.; poloxamers or polyethylene polypropylene copolymers such as Lutrol F grade 68 or 127, poloxamines or other gelling agents such as chitosan, dextran, pectins and natural gums, alone or in combination, may be used as gelling agents in the pharmaceutical composition according to the invention.

These gelling agents make it possible to increase the viscosity of the formulations according to the invention, but may also act as solubilizer.

Carbopol® 980 and/or hydroxypropylcellulose are particularly preferred in the context of the present invention.

The choice of the gelling agent will be made as a function of the pH of the composition defined according to the invention and of the desired viscosity.

According to another advantageous embodiment of the pharmaceutical composition according to the invention, in the presence of certain types of gelling agents, and especially non-preneutralized acrylic polymers, it may contain a neutralizer. The neutralizer/gelling agent ratio is then between 10/1 and 0.1/1, preferably between 7/1 and 0.5/1 and even more preferably between 4/1 and 1/1.

The neutralizer is chosen such that it forms, in the presence of the polymer, salts that are soluble in the vehicle.

The neutralizer is also chosen so as to be able to achieve optimum swelling of the polymer chains during the neutralization of the fillers and the formation of polymer salts.

According to the invention, triethanolamine and/or tromethamine (2-amino-2-hydroxymethyl-1,3-propanediol) are preferably used as neutralizers in the presence of Carbopol® 980. They also make it possible to achieve an optimum viscosity in the pharmaceutical composition according to the invention.

Other neutralizers, for instance sodium hydroxide, ammonium hydroxide, potassium hydroxide, arginine or aminomethylpropanol, may be used in the pharmaceutical composition according to the invention. The neutralizer is chosen as a function of the type of gelling agent used, in a manner known to those skilled in the art.

The active substance(s) present in the pharmaceutical composition according to the invention may advantageously be selected from the group consisting of oestrogens, progestins, androgens, anti-oestrogens and anti-androgens, or mixtures thereof.

The active substance content is advantageously between 0.01% and 5%, these percentages being expressed on a weight basis relative to 100 g of pharmaceutical composition.

The anti-oestrogens may be selected from the group consisting of tamoxifen, 4-hydroxytamoxifen, tamoxifen citrate, toremifen, droloxifen and raloxifen.

The androgens may be selected from the group consisting of the natural androgen, testosterone, and its semi-natural or synthetic derivatives, for instance methyltestosterone; physiological precursors of testosterone such as dehydroepiandrosterone or DHEA, or alternatively prasterone and its derivatives, for instance DHEA sulphate, Δ-4-androstenedione and its derivatives; testosterone metabolites, for instance dihydrotestosterone (DHT) obtained after the enzymatic action of 5-α-reductases; or substances with an androgenic-type effect, such as tibolone.

The anti-androgens may be selected from the group consisting of steroidal compounds such as cyproterone acetate, and medroxyprogesterone, or non-steroidal compounds such as flutamide, nilutamide or bicalutamide. The active substance in the pharmaceutical composition according to the invention is preferably a progestin, an Estrogen or a combination of the two.

Advantageously, the progestin(s) used in the pharmaceutical composition according to the invention may be selected from the group consisting of natural progestins, progesterone or its derivatives of ester type, and synthetic progestins of type 1, 2 or 3. The first group comprises molecules similar to progesterone or the synthetic progestins 1 (SP1) (pregnanes), for example the progesterone isomer (retroprogesterone), medrogesterone, and norprogesterone derivatives (demegestone or promegestone). The second group comprises 17α-hydroxy-progesterone derivatives or synthetic progestins 2 (SP2) (pregnanes), for example cyproterone acetate and medroxyprogesterone acetate. The third group comprises norsteroids or synthetic progestins 3 (SP3), (estranes or norandrostanes). These are 19-nortestosterone derivatives, for example norethindrone. This group also comprises molecules of gonane type, which are derived from these nor-androstanes or estranes and have a methyl group at C18 and an ethyl group at C13. Examples that may be mentioned include norgestimate, desogestrel (3-ketodesogestrel) or gestodene.

Tibolone, which has both progestin and androgenic activity, may also advantageously be selected in the pharmaceutical composition according to the invention.

The oestrogen(s) used in the pharmaceutical composition according to the invention may advantageously be selected from the group consisting of natural oestrogens: 17β-oestradiol, oestrone, equine conjugated oestrogens, estriol and phytoestrogens; semi-natural oestrogens: oestradiol valerate; or else synthetic oestrogens: ethinyl-estradiol; preferably 17β-estradiol.

According to one advantageous embodiment of the pharmaceutical composition according to the invention, the progestin content will be between 0.01% and 5%, preferably between 0.02% and 3% and even more preferably between 0.03% and 1%, these percentages being expressed on a weight basis relative to 100 g of pharmaceutical composition.

According to another particular embodiment of the pharmaceutical composition according to the invention, the oestrogen content will be between 0.01% and 5%, preferably between 0.02% and 3% and even more preferably between 0.03% and 2%, these percentages being expressed on a weight basis relative to 100 g of pharmaceutical composition.

The invention will be understood more clearly with the aid of the non-limiting examples described below.

EXAMPLE 1

Instability of Gels Comprising Oleic Acid

A first series of gels having the compositions given in Table I are subjected to stability tests.
The manufacture of a gel according to the invention is performed as follows:
For 40 kg of a gel manufactured according to formulation E760 containing two active principles, Estradiol (Diosynth) and Progesterone (Xianming):
  26 000 g of 95° ethanol are introduced into a Koruma mixer tank under a vacuum of 800 mbar.
  Next, 2000 g of propylene glycol and 1200 g of oleic acid are successively loaded via the top of the tank, without stirring. The mixture is stirred for at least 5 minutes, with the turbomixer at 2000 rpm and the rotor blade at 40 rpm.
  24.8 g of Estradiol are added. The mixture is then mixed for 15 minutes, with the turbomixer at 2000 rpm and the rotor blade at 40 rpm.
  800 g of progesterone are added. The mixture is then mixed for 15 minutes, with the turbomixer at 2000 rpm and the rotor blade at 40 rpm.
  400 g of Klucel®HF are introduced under a vacuum of 800 mbar, with the turbomixer at 1500 rpm.
  The mixture is stirred for at least 10 minutes, with the turbomixer at 1500 rpm and the rotor blade at 40 rpm.
  Next, purified water is added in an amount sufficient to obtain a total mass of 40 000 g, under a vacuum of 800 mbar, with the rotor blade at 40 rpm.
  The mixture is stirred for at least 10 minutes, with the turbomixer at 1500 rpm and the rotor blade at 40 rpm.
  The turbomixer is switched off.
  A vacuum of 100 mbar is applied for about 2 minutes.
  The mixture is stirred gently for at least 10 minutes, with the rotor blade at 10 rpm.

The other formulations are prepared in the same manner, the amounts of the various components being modified according to Table I.

The oleic acid and ethyl oleate contents were measured, respectively by gas chromatography or by potentiometry (and by potentiometry) after storage at room temperature (25° C.) and 60% relative humidity, at times: 0, 1, 2, 3, 6, 10, 12 and 18 months (and 0, 1, 3, 4, 6, 12, 14 and 20 months for the placebo).

The results are given in Tables II and III.

The specifications or standards given in the tables correspond to the set acceptance criterion which is plus or minus 5% relative to the initial theoretical value. Any value outside this acceptability range is considered non-compliant and corresponds to a "significant" variation. These values are given with grey shading in the tables.

TABLE I

Composition of the aqueous-alcoholic gels tested

| | Samples | | | | |
|---|---|---|---|---|---|
| | E751 placebo | E760 | E761 | E762 | E763 |
| % Progesterone | 0 | 2 | 2 | 3 | 3 |
| % Estradiol | 0 | 0.06 | 0.06 | 0.06 | 0.06 |
| % propylene glycol | 5 | 5 | 5 | 5 | 5 |
| % oleic acid | 2 | 3 | 3 | 2 | 2 |
| % Klucel ®* | 1.5 | 1 | 1.5 | 1 | 1.5 |
| 95% EtOH v/v | 65 | 65 | 65 | 65 | 65 |
| purified water | qs 100 g | qs 100 g | qs 100 g | qs 100 g | qs 100 g |

*Hydroxypropyl cellulose manufactured by the company Aqualon.

An accelerated ageing test was also performed on the same gels which were stored at a temperature of 40° C. with a relative humidity of 75%, at times 0, 1, 2, 3, 4, 5, 6, 10, 11, 12 and 18 months. The oleic acid and ethyl oleate contents were then measured as previously, at the same times. The results are given in Table IV.

Significant esterification of the oleic acid is observed in all the gels during ageing. The content of ethyl oleate formed and the rate of esterification are proportionally higher the larger the starting percentage of oleic acid and the higher the temperature and humidity conditions (difference between 25° C./60% RH and 40° C./75% RH).

This esterification of oleic acid raises two major concerns relating to the integrity of the pharmaceutical specialty product:

- ethyl oleate is sparingly soluble in alcohol, which may lead to an undesired emulsion in the gel;
- since oleic acid has been selected for its role as a percutaneous absorption promoter, a reduction in its content will result in a harmful effect on the percutaneous passage of the active substances.

TABLE II

Change in the oleic acid and ethyl oleate contents over time at 25° C./60% RH as a function of the composition of the gels

| Batches | Tests | Standards | T0 | 1M | 2M | 3M | 6M | 10M | 12M | 18M |
|---|---|---|---|---|---|---|---|---|---|---|
| E 760 | OA as % of gel | 2.9 to 3.2 | 2.9 | 3.1 | 2.9 | 2.9 | 2.8 | | | |
| | OE formed as % of OA | | 0.6 | 1.2 | 2.5 | 3.0 | 5.6 | | | |
| E 761 | OA as % of gel | 2.9 to 3.2 | 2.8 | 3.1 | 2.9 | | | | | |
| | OE formed as % of OA | | 0.6 | 1.1 | 2.3 | | | | | |
| E 762 | OA as % of gel | 1.9 to 2.1 | 2.0 | 2.1 | 1.9 | 2.0 | | | | |
| | OE formed as % of OA | | 0.4 | 1.0 | 1.7 | 2.6 | | | | |
| E 763 | OA as % of gel | 1.9 to 2.1 | 1.9 | 2.0 | 1.9 | 1.9 | 1.9 | | | |
| | OE formed as % of OA | | 0.4 | 0.9 | 1.6 | 2.5 | 4.5 | | | |

TABLE III

Change in the oleic acid and ethyl oleate contents over time at 25° C./60% RH on the placebo gel

| BATCHES | Tests | Standards | T0 | 1M | 3M | 4M | 6M | 12M | 14M | 20M |
|---|---|---|---|---|---|---|---|---|---|---|
| E 751 | OA as % of gel | 1.9 to 2.1 | 1.8 | 1.9 | 1.9 | 1.9 | | | | |
| Placebo | OE formed as % of OA | | NP* | 3.0 | 2.9 | 3.4 | | | | |

*NP: not performed

TABLE IV

Change in the oleic acid and ethyl oleate contents over time at 40° C./75% RH as a function of the composition of the gels

| Batches | Tests | Standards | T0 | 1M | 2M | 3M | 4M | 5M | 6M | 10M | 11M | 12M | 18M |
|---|---|---|---|---|---|---|---|---|---|---|---|---|---|
| E 760 | OA as % of gel | 2.9 to 3.2 | 2.9 | 2.9 | | | | | | | | | |
| | OE formed as % of OA | | 0.6 | 3.9 | | | | | | | | | |
| E 761 | OA as % of gel | 2.9 to 3.3 | 2.8 | 3.0 | | | | | | | | | |
| | OE formed as % of OA | | 0.6 | 3.7 | | | | | | | | | |
| E 762 | OA as % of gel | 1.9 to 2.1 | 2.0 | 2.0 | | | | | | | | | |
| | OE formed as % of OA | | 0.4 | 2.7 | | | | | | | | | |

TABLE IV-continued

Change in the oleic acid and ethyl oleate contents over time at 40° C./75% RH as a function of the composition of the gels

| Batches | Tests | Standards | T0 | 1M | 2M | 3M | 4M | 5M | 6M | 10M | 11M | 12M | 18M |
|---|---|---|---|---|---|---|---|---|---|---|---|---|---|
| E 763 | OA as % of gel | 1.9 to 2.1 | 1.9 | 1.9 | 1.9 | ▓ | ▓ | ▓ | ▓ | ▓ | ▓ | ▓ | ▓ |
| | OE formed as % of OA | | 0.4 | 2.4 | 1.3 | ▓ | ▓ | ▓ | ▓ | ▓ | ▓ | ▓ | ▓ |

THE GREY SHADING SHOULD BE REMOVED FROM BATCH E762 at 6.6% EO.

EXAMPLE 2

Instability of Gels Comprising Oleic Acid and Stabilization Thereof According to the Invention A second series of gels having the compositions given in Table V was subjected to stability tests.

The manufacture of a gel according to the invention is performed as follows:

Specifically, for 30 kg of a gel manufactured according to the formulation E844 containing two active principles Estradiol (Diosynth) and Progesterone (Xianming):

19 500 g of 95° ethanol are placed in a Koruma mixer tank under a vacuum of 800 mbar.

Next, 1500 g of propylene glycol and 1500 g of oleic acid are successively loaded via the top of the tank, without stirring. The mixture is stirred for at least 5 minutes, with the turbomixer at 2000 rpm and the rotor blade at 40 rpm.

18.6 g of Estradiol are added. Next, the mixture is stirred for 15 minutes, with the turbomixer at 2000 rpm and the rotor blade at 40 rpm.

600 g of Progesterone are added. The mixture is then stirred for 15 minutes, with the turbomixer at 2000 rpm and the rotor blade at 40 rpm.

300 g of Klucel®HF are introduced under a vacuum of 800 mbar, with the turbomixer at 1500 rpm.

The mixture is stirred for at least 10 minutes, with the turbomixer at 1500 rpm and the rotor blade at 40 rpm.

Next, purified water is added in an amount sufficient for 30 000 g, under a vacuum of 800 mbar, with the rotor blade at 40 rpm.

The mixture is stirred for at least 10 minutes, with the turbomixer at 1500 rpm and the rotor blade at 40 rpm.

The turbomixer is switched off.

A vacuum of 100 mbar is applied for about 2 minutes.

The mixture is stirred gently for at least 10 minutes, with the rotor blade at 10 rpm.

The other formulations E 845 to E 854 were prepared in the same manner, the amounts of compounds introduced being varied according to Table V.

Samples E858 to E865 contain a pH 10.7 carbonate/bicarbonate buffer. This buffer is loaded in place of the purified water during the preparation of the gel according to the invention. It was prepared in the following manner:

0.2M solution of anhydrous $Na_2CO_3$ in purified water, ie: 21.2 g/l (Solution A), was prepared.

A 0.2M solution of $NaHCO_3$ in purified water, ie: 16.8 g/l (solution B), was prepared.

21.3 ml of solution A were then added to 3.8 ml of solution B and water was added to obtain 100 ml. The resulting solution corresponds to the buffer used in tests E858 to E 865. The pH of this buffer solution is 10.7.

The specifications or standards given in the tables correspond to the set acceptance criterion, which is plus or minus 5% relative to the initial theoretical value. Any value outside this acceptability range is considered non-compliant and corresponds to a "significant" variation. These values are given with grey shading in the tables.

The gels were stored at 25° C. and 60% relative humidity, and at 40° C. and 75% relative humidity (accelerated ageing). The oleic acid and ethyl oleate contents were measured as previously, at times: 0, 1, 2, 3 and 6 months. The results are given in Table VI (25° C./60% RH) and VII (40° C./75% RH).

These analyses demonstrate that the use of the carbonate/bicarbonate buffer at pH 10.7 significantly reduces the esterification of oleic acid to ethyl oleate.

TABLE V

Composition of the aqueous-alcoholic gels E844 to 865

| | Progesterone % | Estradiol % | Polypropylene Glycol % | Oleic acid % | KLUCEL[a] % | ETOH 95% V/V % | Isopropanol % | qs 100 g |
|---|---|---|---|---|---|---|---|---|
| E 844 | 2 | 0.06 | 5 | 5 | 1 | 65 | 0 | water |
| E*845 | 2 | 0.06 | 5 | 5 | 1 | 65 | 0 | water |
| E 846 | 3 | 0.06 | 5 | 5 | 1 | 65 | 0 | water |
| E*847 | 3 | 0.06 | 5 | 5 | 1 | 65 | 0 | water |
| E 848 | 3 | 0.06 | 5 | 5 | 1.5 | 65 | 0 | water |
| E*849 | 3 | 0.06 | 5 | 5 | 1.5 | 65 | 0 | water |
| E 850 | 3 | 0.06 | 5 | 2 | 1 | 65 | 0 | water |
| E*851 | 3 | 0.06 | 5 | 2 | 1 | 65 | 0 | water |
| E 852 | 2 | 0.06 | 5 | 5 | 1.5 | 65 | 0 | water |
| E*853 | 2 | 0.06 | 5 | 5 | 1.5 | 65 | 0 | water |
| E 854 | 3 | 0.06 | 5 | 2 | 1.5 | 65 | 0 | water |
| E*855 | 3 | 0.06 | 5 | 2 | 1.5 | 65 | 0 | water |
| E 858 | 2 | 0.06 | 5 | 5 | 1 | 65 | 0 | buffer |
| E*859 | 2 | 0.06 | 5 | 5 | 1 | 65 | 0 | buffer |
| E 861 | 3 | 0.06 | 5 | 2 | 1 | 65 | 0 | buffer |

TABLE V-continued

Composition of the aqueous-alcoholic gels E844 to 865

| | Progesterone % | Estradiol % | Polypropylene Glycol % | Oleic acid % | KLUCEL[a] % | ETOH 95% V/V % | Isopropanol % | qs 100 g |
|---|---|---|---|---|---|---|---|---|
| E*862 | 3 | 0.06 | 5 | 2 | 1 | 65 | 0 | buffer |
| E 863 | 3 | 0.06 | 5 | 5 | 1 | 65 | 0 | buffer |
| E*864 | 3 | 0.06 | 5 | 5 | 1 | 65 | 0 | buffer |
| E 865 | 5 | 0.06 | 5 | 3 | 1 | 30 | 35 | buffer |

[a]Hydroxypropyl cellulose manufactured by the company Aqualon.
*Supplier = SCHERING - for the other batches, supplier = DIOSYNTH

TABLE VI (part 1):
Change in the oleic acid and ethyl oleate
contents over time at 25° C./60% RH as a function of the
composition of the gels (gels without stabilizer)

| BATCHES | Tests | Standards | T0 | 2 M | 3 M | 6 M |
|---|---|---|---|---|---|---|
| E 844 | Oleic acid in g/100 g gel | 4.8 to 5.3 | 4.9 | 4.8 | 4.7 | 4.6 |
| | Ethyl oleate formed in g/100 g OA | | 2.3 | 8.4 | 11.9 | 16.2 |
| E 845 | Oleic acid in g/100 g gel | 4.8 to 5.3 | 5.0 | 4.8 | 4.7 | 4.6 |
| | Ethyl oleate formed in g/100 g OA | | 2.06 | 8.1 | 11.4 | 15.8 |
| E 846 | Oleic acid in g/100 g gel | 4.8 to 5.3 | 5.0 | 4.8 | 4.7 | 4.6 |
| | Ethyl oleate formed in g/100 g OA | | 2.0 | 7.8 | 10.5 | 14.7 |
| E 847 | Oleic acid in g/100 g gel | 4.8 to 5.3 | 5.0 | 4.8 | 4.7 | 4.6 |
| | Ethyl oleate formed in g/100 g OA | | 1.8 | 7.5 | 10.5 | 14.9 |
| E 848 | Oleic acid in g/100 g gel | 4.8 to 5.3 | 5.0 | 4.9 | 4.8 | 4.6 |
| | Ethyl oleate formed in g/100 g OA | | 1.8 | 7.0 | 9.9 | 13.8 |
| E 849 | Oleic acid in g/100 g gel | 4.8 to 5.3 | 5.0 | 5.00 | 4.8 | 4.7 |
| | Ethyl oleate formed in g/100 g OA | | 1.60 | 6.7 | 9.9 | 13.7 |
| E 850 | Oleic acid in g/100 g gel | 1.9 to 2.1 | 2.0 | 2.0 | 2.0 | 2.0 |
| | Ethyl oleate formed in g/100 g OA | | 0.8 | 4.3 | 5.6 | 6.6 |
| E 851 | Oleic acid in g/100 g gel | 1.9 to 2.1 | 2.0 | 2.0 | 2.0 | 2.0 |
| | Ethyl oleate formed in g/100 g OA | | 0.50 | 4.3 | 5.4 | 6.7 |
| E 852 | Oleic acid in g/100 g gel | 4.8 to 5.3 | 4.9 | 4.8 | 4.7 | 4.7 |
| | Ethyl oleate formed in g/100 g OA | | 1.8 | 7.6 | 10.2 | 14.6 |
| E 853 | Oleic acid in g/100 g gel | 4.8 to 5.3 | 5.0 | 4.8 | 4.7 | 4.6 |
| | Ethyl oleate formed in g/100 g OA | | 1.6 | 7.2 | 10.2 | 14.9 |
| E 854 | Oleic acid in g/100 g gel | 1.9 to 2.1 | 2.0 | 2.0 | 1.9 | 2.0 |
| | Ethyl oleate formed in g/100 g OA | | 0.63 | 3.9 | 4.9 | 6.0 |
| E 855 | Oleic acid in g/100 g gel | 1.9 to 2.1 | 2.0 | 2.0 | 2.0 | 2.0 |
| | Ethyl oleate formed in g/100 g OA | | 0.50 | 4.0 | 4.6 | 6.1 |

(part 2):
Change in the oleic acid and ethyl oleate
contents over time at 25° C./60% RH as a function of the
composition of the gels (gels with stabilizer)

| BATCHES | Tests | Standards | T0 | 2 M | 3 M | 6 M |
|---|---|---|---|---|---|---|
| E 858 | Oleic acid in g/100 g gel | 4.3 to 5.7 | 4.5 | 4.5 | 4.4 | 4.5 |
| | Ethyl oleate formed in g/100 g OA | | 0.31 | 2.3 | 2.5 | 4.3 |
| E 859 | Oleic acid in g/100 g gel | 4.3 to 5.7 | 4.6 | 4.5 | 4.4 | 4.4 |
| | Ethyl oleate formed in g/100 g OA | | 0.4 | 2.5 | 2.6 | 4.3 |
| E 861 | Oleic acid in g/100 g gel | 1.4 to 1.6 | 1.5 | 1.5 | 1.4 | 1.4 |
| | Ethyl oleate formed in g/100 g OA | | 0 | 1.3 | trace | trace |
| E 862 | Oleic acid in g/100 g gel | 1.4 to 1.6 | 1.5 | 1.5 | 1.4 | 1.4 |
| | Ethyl oleate formed in g/100 g OA | | 0 | 1.3 | 0.1 | trace |
| E 863 | Oleic acid in g/100 g gel | 4.3 to 5.7 | 4.4 | 4.5 | 4.4 | 4.5 |
| | Ethyl oleate formed in g/100 g OA | | 0.2 | 2.5 | 2.5 | 3.8 |
| E 864 | Oleic acid in g/100 g gel | 4.3 to 5.7 | 4.4 | 4.5 | 4.5 | 4.5 |
| | Ethyl oleate formed in g/100 g OA | | 0.3 | 2.2 | 2.4 | 3.8 |
| E 865 | Oleic acid in g/100 g gel | 2.4 to 2.6 | 2.5 | 2.6 | 2.5 | 2.5 |
| | Ethyl oleate formed in g/100 g OA | | 0 | 0.9 | trace | trace |

TABLE VII

Change in the oleic acid and ethyl oleate contents over time at 40° C./75% RH as a function of the composition of the gels (gels without stabilizer)

| BATCHES | Tests | Standards | T0 | 2M | 3M | 6M |
|---|---|---|---|---|---|---|
| E 844 | Oleic acid in g/100 g gel | 4.8 to 5.3 | 5.0 | 4.5 | 3.9 | 4.0 |
|  | Ethyl oleate formed in g/100 g OA |  | 2.3 | 14.4 | 25.9 | 37.2 |
| E 845 | Oleic acid in g/100 g gel | 4.8 to 5.3 | 5.0 | 4.6 | 4.3 | 4.0 |
|  | Ethyl oleate formed in g/100 g OA |  | 2.06 | 13.5 | 22.2 | 35.5 |
| E 846 | Oleic acid in g/100 g gel | 4.8 to 5.3 | 5.0 | 4.6 | 4.3 | 4.0 |
|  | Ethyl oleate formed in g/100 g OA |  | 2.0 | 14.1 | 21.6 | 34.7 |
| E 847 | Oleic acid in g/100 g gel | 4.8 to 5.3 | 5.0 | 4.6 | 4.3 | 4.1 |
|  | Ethyl oleate formed in g/100 g OA |  | 1.81 | 12.4 | 20.5 | 34.5 |
| E 848 | Oleic acid in g/100 g gel | 4.8 to 5.3 | 5.0 | 4.6 | 4.3 | 4.1 |
|  | Ethyl oleate formed in g/100 g OA |  | 1.8 | 11.6 | 19.2 | 33.7 |
| E 849 | Oleic acid in g/100 g gel | 4.8 to 5.3 | 5.0 | 4.6 | 4.0 | 4.1 |
|  | Ethyl oleate formed in g/100 g OA |  | 1.6 | 11.4 | 20.9 | 33.9 |
| E 850 | Oleic acid in g/100 g gel | 1.9 to 2.1 | 2.0 | 2.0 | 1.9 | 1.8 |
|  | Ethyl oleate formed in g/100 g OA |  | 0.8 | 7.3 | 11.1 | 19.0 |
| E 851 | Oleic acid in g/100 g gel | 1.9 to 2.1 | 2.0 | 1.9 | 1.9 | 1.8 |
|  | Ethyl oleate formed in g/100 g OA |  | 0.50 | 7.5 | 11.2 | 18.5 |
| E 852 | Oleic acid in g/100 g gel | 4.8 to 5.3 | 4.9 | 4.5 | 4.3 | 4.0 |
|  | Ethyl oleate formed in g/100 g OA |  | 1.8 | 12.5 | 20.7 | 34.6 |
| E 853 | Oleic acid in g/100 g gel | 4.8 to 5.3 | 5.0 | 4.6 | 4.3 | 4.1 |
|  | Ethyl oleate formed in g/100 g OA |  | 1.6 | 13.0 | 19.8 | 35.6 |
| E 854 | Oleic acid in g/100 g gel | 1.9 to 2.1 | 2.0 | 2.0 | 2.0 | 1.8 |
|  | Ethyl oleate formed in g/100 g OA |  | 0.63 | 6.3 | 9.8 | 17.1 |
| E 855 | Oleic acid in g/100 g gel | 1.9 to 2.1 | 2.0 | 1.9 | 1.8 | 1.8 |
|  | Ethyl oleate formed in g/100 g OA |  | 0.5 | 7.0 | 10.3 | 17.0 |

TABLE VII-continued

Change in the oleic acid and ethyl oleate contents over time at 40° C./75% RH as a function of the composition of the gels (gels with stabilizer)

| BATCHES | Tests | Standards | T0 | 2M | 3M | 6M |
|---|---|---|---|---|---|---|
| E 858 | Oleic acid in g/100 g gel | 4.3 to 5.7 | 4.5 | 4.4 | 4.3 | 4.3 |
|  | Ethyl oleate formed in g/100 g OA |  | 0.31 | 4.0 | 5.9 | 11.5 |
| E 859 | Oleic acid in g/100 g gel | 4.3 to 5.7 | 4.6 | 4.5 | 4.3 | ▓ |
|  | Ethyl oleate formed in g/100 g OA |  | 0.4 | 4.3 | 6.1 | ▓ |
| E 861 | Oleic acid in g/100 g gel | 1.4 to 1.6 | 1.50 | 1.5 | 1.4 | 1.5 |
|  | Ethyl oleate formed in g/100 g OA |  | 0 | 1.9 | 1.1 | 1.4 |
| E 862 | Oleic acid in g/100 g gel | 1.4 to 1.6 | 1.50 | 1.4 | 1.4 | 1.4 |
|  | Ethyl oleate formed in g/100 g OA |  | 0 | 2.0 | 1.2 | 1.4 |
| E 863 | Oleic acid in g/100 g gel | 4.3 to 5.7 | 4.4 | 4.5 | 4.3 | 4.4 |
|  | Ethyl oleate formed in g/100 g OA |  | 0.2 | 4.3 | 5.9 | 11.3 |
| E 864 | Oleic acid in g/100 g gel | 4.3 to 5.7 | 4.4 | 4.5 | 4.4 | 4.3 |
|  | Ethyl oleate formed in g/100 g OA |  | 0.3 | 4.2 | 6.2 | 11.2 |
| E 865 | Oleic acid in g/100 g gel | 2.4 to 2.6 | 2.50 | 2.5 | 2.5 | 2.5 |
|  | Ethyl oleate formed in g/100 g OA |  | 0 | 1.3 | 0.3 | 1.2 |

The invention claimed is:

1. A pharmaceutical composition for transdermal or transmucous administration of at least one active substance, comprising
an active substance,
a fatty acid percutaneous absorption promoter in an amount of between 0.1% and 20%, these percentages being expressed on a weight basis relative to 100 g of pharmaceutical composition,
an alcoholic vehicle comprising an alcohol selected from the group consisting of ethanol and isopropanol, and
a stabilizer capable of stabilizing the fatty acid in said pharmaceutical composition, wherein said stabilizer comprises the fatty acid ester of said fatty acid and said alcohol and is present in an amount of between 0.1% and 10%, these percentages being expressed on a weight basis relative to 100 g of pharmaceutical composition and
wherein said composition is in the form of a gel or solution, and
wherein the amount of said fatty acid percutaneous absorption promoter does not vary by more than +/−5% after storage for 6 months at 40° C. and 75% relative humidity.

2. A pharmaceutical composition according to claim 1, wherein the fatty acid is selected from the group consisting of capric acid, lauric acid, myristic acid, palmitic acid, stearic acid, oleic acid, palmitoleic acid, linoleic acid and linolenic acid.

3. A pharmaceutical composition according to claim 1, having a pH of between 4 and 10.

4. A pharmaceutical composition according to claim 1, wherein the fatty acid ester is selected from the group consisting of ethyl oleate, isopropyl oleate, isopropyl myristate, isopropyl palmitate, ethyl octanoate, ethyl dodecanoate, ethyl linoleate and ethyl linolenate.

5. A pharmaceutical composition according to claim 1, wherein the alcoholic vehicle comprises ethanol.

6. A pharmaceutical composition according to claim 1, having an alcoholic vehicle content of between 10% and 90%, these percentages being expressed on a weight basis relative to 100 g of pharmaceutical composition.

7. A pharmaceutical composition according to claim 1, further comprising a co-solvent selected from the group consisting of glycerol, propylene glycol, polyethylene glycol, and mixtures thereof.

8. A pharmaceutical composition according to claim 7, having a co-solvent content of between 0.5% and 20% these percentages being expressed on a weight basis relative to 100 g of pharmaceutical composition.

9. A pharmaceutical composition according to claim 1, being in the form of a gel, and further comprising between 0.2% and 30% of a gelling agent, these percentages being expressed on a weight basis relative to 100 g of pharmaceutical composition.

10. A pharmaceutical composition according to claim 9, wherein the gelling agent is selected from the group consisting of carbomers, non-preneutralized acrylic polymers, cellulose derivatives, poloxamers, poloxamines, chitosan, dextran pectins, natural gums, and mixtures thereof.

11. A pharmaceutical composition according to claim 9, further comprising a neutralizer.

12. A pharmaceutical composition according to claim 11, wherein the neutralizer is selected from the group consisting of triethanolamine, sodium hydroxide, ammonium hydroxide, potassium hydroxide, arginine, aminomethylpropanol and tromethamine, and mixtures thereof.

13. A pharmaceutical composition according to claim 11, wherein the neutralizer/gelling agent ratio is between 10/1 and 0.1/1.

14. A pharmaceutical composition according to claim 1, wherein the active substance is selected from the group consisting of oestrogens, progestins, androgens, anti-oestrogens and anti-androgens, or mixtures thereof.

15. A pharmaceutical composition according to claim 14, having an active substance content of between 0.01% and 5%, these percentages being expressed on a weight basis relative to 100 g of pharmaceutical composition.

16. A pharmaceutical composition according to claim 1, having a fatty acid content of between 0.2% and 10%, these percentages being expressed on a weight basis relative to 100 g of pharmaceutical composition.

17. A pharmaceutical composition according to claim 1, having a fatty acid content of between 0.5% and 5%, these percentages being expressed on a weight basis relative to 100 g of pharmaceutical composition.

18. A pharmaceutical composition according to claim 1, having a pH of between 5 and 9.

19. A pharmaceutical composition according to claim 1, having a pH of between 6 and 8.

20. A pharmaceutical composition according to claim 1, having a fatty acid ester content of between 0.2% and 5%, these percentages being expressed on a weight basis relative to 100 g of pharmaceutical composition.

21. A pharmaceutical composition according to claim 1, having a fatty acid ester content of between 0.5% and 2.5%, these percentages being expressed on a weight basis relative to 100 g of pharmaceutical composition.

22. A pharmaceutical composition according to claim 1, having an alcoholic vehicle content of between 20% and 80%, these percentages being expressed on a weight basis relative to 100 g of pharmaceutical composition.

23. A pharmaceutical composition according to claim 1, having an alcoholic vehicle content of between 40% and 70%, these percentages being expressed on a weight basis relative to 100 g of pharmaceutical composition.

24. A pharmaceutical composition according to claim 7, having a co-solvent content of between 1% and 10%, these percentages being expressed on a weight basis relative to 100 g of pharmaceutical composition.

25. A pharmaceutical composition according to claim 1, being in the form of a gel, and-further comprising between 0.5% and 10% of a gelling agent, these percentages being expressed on a weight basis relative to 100 g of pharmaceutical composition.

26. A pharmaceutical composition according to claim 1, being in the form of a gel, and-further comprising between 0.3% and 5% of a gelling agent, these percentages being expressed on a weight basis relative to 100 g of pharmaceutical composition.

27. A pharmaceutical composition according to claim 9, wherein the gelling agent is selected from the group consisting of carbomers, cellulose derivatives, and mixtures thereof.

28. A pharmaceutical composition according to claim 9, wherein the gelling agent is selected from the group consisting of Carbopol® 980, hydroxypropylcellulose and mixtures thereof.

29. A pharmaceutical composition according to claim 11, wherein the neutralizer is selected from the group consisting of triethanolamine, tromethamine, and mixtures thereof.

30. A pharmaceutical composition according to claim 11, wherein the neutralizer/gelling agent ratio is between 7/1 and 0.5/1.

31. A pharmaceutical composition according to claim 11, wherein the neutralizer/gelling agent ratio is between 4/1 and 1/1.

32. A pharmaceutical composition for transdermal or transmucous administration of at least one active substance, comprising
   an active substance,
   oleic acid in an amount of between 0.1% and 20%, these percentages being expressed on a weight basis relative to 100 g of pharmaceutical composition,
   an alcoholic vehicle comprising ethanol, and
   ethyl oleate in an amount of between 0.1% and 10%, these percentages being expressed on a weight basis relative to 100 g of pharmaceutical composition,
   wherein said composition is in the form of a gel or solution, and wherein the amount of oleic acid does not vary by more than +/−5% after storage for 6 months at 40° C. and 75% relative humidity.

33. A method of making a pharmaceutical composition for transdermal or transmucous administration of at least one active substance, comprising admixing:
   an active substance,
   a fatty acid percutaneous absorption promoter in an amount of between 0.1% and 20%, these percentages being expressed on a weight basis relative to 100 g of pharmaceutical composition,
   an alcoholic vehicle comprising an alcohol selected from the group consisting of ethanol and isopropanol, and
   a stabilizer capable of stabilizing the fatty acid in said pharmaceutical composition, wherein said stabilizer comprises the fatty acid ester of said fatty acid and said alcohol and is present in an amount of between 0.1% and 10%, these percentages being expressed on a weight basis relative to 100 g of pharmaceutical composition,
   wherein said composition is in the form of a gel or solution.

34. A pharmaceutical composition made by a method according to claim 33.

* * * * *

UNITED STATES PATENT AND TRADEMARK OFFICE
CERTIFICATE OF CORRECTION

PATENT NO. : 7,611,727 B2  Page 1 of 1
APPLICATION NO. : 10/436380
DATED : November 3, 2009
INVENTOR(S) : Taravella et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 566 days.

Delete the phrase "by 566 days" and insert -- by 1159 days --

Signed and Sealed this

Eighth Day of June, 2010

David J. Kappos
*Director of the United States Patent and Trademark Office*